United States Patent [19]

Sunshine et al.

[11] Patent Number: 4,722,938
[45] Date of Patent: Feb. 2, 1988

[54] METHODS FOR USING MUSCULOSKELETAL RELAXANTS

[75] Inventors: Abraham Sunshine, New York; Eugene M. Laska, Larchmont; Carole E. Siegel, Mamaroneck, all of N.Y.

[73] Assignee: Analgesic Associates, Larchmont, N.Y.

[21] Appl. No.: 815,502

[22] Filed: Jan. 2, 1986

Related U.S. Application Data

[63] Continuation of Ser. No. 686,380, Dec. 26, 1984, abandoned.

[51] Int. Cl.$^4$ ...................... A61K 31/19; A61K 31/27
[52] U.S. Cl. ...................................... 514/479; 514/568
[58] Field of Search .............................. 514/568, 479

[56] References Cited

FOREIGN PATENT DOCUMENTS 2121529 12/1971 France .

OTHER PUBLICATIONS

Armas & Valencia, "Eficacia Terapeutica de la Asociacion Naproxen-Carisoprodol en Ciertas Enfermedader Musculoesqueleticas"[Therapeutic Effectiveness of Naproxen-Carisoprodol Association in Certain Musculoskeletal Disorders], in *Investigation Medica Internacional,* pp. 350–356, (1983), and English translation thereof.
Goti & Valencia, "Caracterizacion Clinica de Una Nueva Asociacion (Naproxen + Carisoprodol) en Padecimientos del Aparato Musculoesqueletico"[Clinical Description of a New Association (Naproxen + Carisoprodol) in Ailments of the Musculoskeletal Apparatus], *Investigation Medica Internacional,* pp. 475–478, (1983), and English translation thereof.
Socialist Republic of Romania Description of Invention 82,717, copy of patent and English translation thereof; (10/83).
Rego, "Mio-Relaxantes No Tratmento Das Lombalgias Agudas E Das Lombo-Ciaticas Recentes"[Muscle Relaxants in the Treatment of Acute Lumbalgias and Recent Lumbo–Sciatica Cases], *Acta Reumatologica Portuguesa,* II, 2:363–364, (1974), copy of the original and English translation thereof.
Schror, "Analgetisch-Antiphlogistische Therapie Von Schmerzzustanden des Bewegungsapparates"[Analgesic-Antiphlogistic Therapy of Locomotor System Pain], *Therapiewoche,* 28, 5657–5663, (1978), copy of the original and English translation thereof.
Schar, "Medikamentose Behandlung von Lumboischialgien"[Drug Treatment of the Lumbago-Sciatic Syndrome], *Schweiz. Rundschau Med. (Praxis),* vol. 68, No. 5, pp. 141–142, (Jan. 30, 1979), copy of original article and English translation thereof.
Kolodny and Klipper, "Bone and Joint Diseases in the Elderly", *Hospital Practice,* pp. 91–101, (Nov. 1976).
Nascimento, "Use of an Association Containing an Analgesic, a Muscle Relaxant and Vitamin B Complex in Degenerative Joint Diseases, Extra-Articular Rheumatic Ailments and Traumatic Afflictions", *F med,* (BR), 83(3):361–363, (1981), original article and English translation thereof.
Repschlaeger and McPherson, "Classification, Mechanism and Management of Headache", *Clinical Pharmacy,* vol. 3, pp. 139–150, (Mar.–Apr. 1984).

*Primary Examiner*—Stanley J. Friedman
*Attorney, Agent, or Firm*—Burns, Doane, Swecker & Mathis

[57] ABSTRACT

Novel pharmaceutical analgesic, anti-inflammatory and skeletal muscle relaxant compositions and methods of using same comprising an analgesically and anti-inflammatory effective amount of at least one non-steroidal anti-inflammatory drug other than aspirin, acetaminophen and phenacetin, in combination with an effective amount of a skeletal muscle relaxant.

19 Claims, No Drawings

METHODS FOR USING MUSCULOSKELETAL RELAXANTS

This application is a continuation of application Ser. No. 686,380, filed Dec. 26, 1984, now abandoned.

BACKGROUND OF THE INVENTION

1. Field of the Invention

The present invention relates generally to novel pharmaceutical compositions of matter comprising one or more non-steroidal anti-inflammatory drugs in combination with at least one skeletal muscle relaxant, and to methods of using said compositions in the treatment of a variety of skeletal muscle disorders including skeletal muscle spasms, certain orthopedic conditions, disk syndromes, low back pain and the like.

2. Description of the Prior Art

Centrally acting skeletal muscle relaxants are generally prescribed either as single agents or as components of combination products. The Food and Drug Administration has approved indications for these medications as adjuncts to rest and physical therapy for relief of acute, painful musculoskeletal problems. Clinically, the mild pain associated with the majority of cases of minor muscle strains and minor injuries is self limiting. Most patients usually respond rapidly to rest. An anti-inflammatory drug may be useful when there is considerable tissue damage and edema. On the other hand, severe musculoskeletal strains and sprains, trauma, and cervical or lumbar radiculopathy as a consequence of degenerative osteoarthritis, herniated disk, spondylitis or laminectomy, often cause moderate or severe and more chronic painful skeletal muscle spasm. The principal symptoms include local pain, tenderness on palpation, increased muscle consistency and limitation of motion. For these patients skeletal muscle relaxants alone or in combination with an analgesic are frequently prescribed. Results of some studies have suggested that a formulation of a muscle relaxant and an analgesic provides greater benefit in patients with acute musculoskeletal problems than similar doses of an analgesic alone.

Table I lists several commercial combinations available. A current commercial muscle relaxant formulation is Soma® Compound by Carter-Wallace, Inc. which contains 200 mg carisoprodol and 325 mg aspirin. Carisoprodol is a centrally-acting muscle relaxant that does not directly relax tense skeletal muscles in man. Aspirin is a conventional non-narcotic analgesic with anti-inflammatory and antipyretic activity. The most common adverse reactions associated with the use of aspirin in this product have been gastrointestinal, including nausea, vomiting, gastritis, occult bleeding, constipation and diarrhea. Allergic type reactions associated with aspirin may also involve the respiratory tract and skin.

Another commercial skeletal muscle relaxant formulation is Parafon Forte® by McNeil Pharmaceutical. Parafon Forte contains 250 mg chlorzoxazone and 300 mg acetaminophen. Chlorzoxazone is a centrally-acting agent which does not directly relax tense skeletal muscles in man. Acetaminophen, a nonsalicylate analgesic, is a conventional non-narcotic analgesic with antipyretic activity.

Robaxisal® by A. H. Robins Company, Inc. is another commercial muscle relaxant formulation which contains 400 mg methocarbamol and 325 mg aspirin. The mechanism of action of methocarbamol in humans has not been established, but may be due to general central nervous system depression. Methocarbamol does not directly relax tense skeletal muscles in man. Adverse reactions that have been associated with aspirin in this formulation include: nausea and other gastrointestinal discomfort, gastritis, gastric erosion, vomiting, constipation, diarrhea, angioedema, asthma, rash, pruritis and urticaria.

Norgesic® and Norgesic® Forte are commercial products by Riker Laboratories, Inc. that contain a muscle relaxant, aspirin and caffeine. The specific formulation for Norgesic is 25 mg orphenadrine citrate, 385 mg aspirin and 30 mg caffeine. Norgesic Forte contains 50 mg orphenadrine citrate, 770 mg aspirin and 60 mg caffeine. Orphenadrine citrate is 2-dimethylaminoethyl 2-methylbenzhydryl ether citrate. The common side effects and concerns associated with the use of aspirin occur with the use of Norgesic and Norgesic Forte as well.

TABLE I

Some Combination Products Containing a Skeletal Muscle Relaxant

| TRADENAME | CONTENTS OF A SINGLE TABLET | | | | TYPICAL DOSAGE PRESENTED AS NO. OF TABLETS |
|---|---|---|---|---|---|
| | SKELETAL MUSCLE RELAXANT | | ADDITIONAL INGREDIENTS | | |
| SOMA COMPOUND | Carisoprodol | 200 mg | aspirin | 325 mg | 1-2 |
| SOMA COMPOUND WITH CODEINE | Carisoprodol | 200 mg | aspirin codeine PO4 | 325 mg 16 mg | 1-2 |
| PARAFON FORTE | Chlorzoxazone | 250 mg | acetaminophen | 300 mg | 1-2 |
| ROBAXISAL | Methocarbamol | 400 mg | aspirin | 325 mg | 2 |
| NORGESIC | Orphenadrine Citrate | 25 mg | aspirin caffeine | 385 mg 30 mg | 1-2 |
| NORGESIC FORTE | Orphenadrine Citrate | 50 mg | aspirin caffeine | 770 mg 60 mg | ½-1 |

At the present time, one commercial product, Parafon Forte, a skeletal muscle relaxant formulation containing acetaminophen, will be the subject of a hearing granted by the Commissioner of Food and Drugs on a proposal to withdraw approval of its new drug application sometime in 1985. The Director of the Bureau of Drugs of the FDA in a notice published in the Federal Register, 1982, 47 F.R. 22599 concluded that he was unaware of any adequate and well-controlled clinical investigation conducted by experts qualified by scientific training and experience . . . [that] demonstrates the effectiveness of Parafon Forte. The present position of the Commissioner of Food and Drugs is set forth below [Federal Register, 1984, 49(200): 48212–48214]:

> Approval of this NDA will be withdrawn unless there exists substantial evidence that Parafon Forte has the clinical effect that it purports or is represented to have under the conditions of use prescribed, recommended, or suggested in its labeling
...."

It should be noted that all of the previously described skeletal muscle relaxant/non-narcotic analgesic formulations include either aspirin or acetaminophen as the non-narcotic analgesic agent. However, a number of alternative non-narcotic agents offering a variety of advantages over these conventionally employed nonnarcotic analgesic antipyretics have now been developed. These newer non-steriodal anti-inflammatory drugs are widely administered orally in the treatment of mild to severe pain, as well as for a variety of disorders including rheumatoid and osteoarthritis. Within this class of drugs, the compounds vary widely in their chemical structure and their biological profiles as analgesics, anti-inflammatory agents and antipyretic agents. The principal advantages of these new non-steroidal anti-inflammatory drugs include not only the clinically superior analgesic and anti-inflammatory activity of these agents compared to aspirin, acetaminophen or phenacetin, but also a lessening of the adverse side effects experienced with these conventional agents; more specifically, the gastrointestinal ulcerations and bleeding experienced with aspirin and the hepatic toxicity prevalent with the use of large doses of acetaminophen.

While aspirin and acetaminophen have been utilized in those previous compositions, it has not been heretofore proposed to use any of the newer non-steroidal anti-inflammatory drugs (i.e. excluding aspirin, acetaminophen and phenactin) in combination with skeletal muscle relaxants to achieve more pain relief, a lesser incidence of side effects and thereby a more effective treatment of the musculoskeletal disorder.

SUMMARY OF THE INVENTION

Surprisingly, the present inventors now find that, the newer non-steroidal anti-inflammatory drugs, which differ substantially in chemical structure from aspirin, acetaminophen and phenacetin, and which have significantly different biological profiles therefrom can be advantageously formulated into a novel composition together with a skeletal muscle relaxant and administered to mammals, especially to humans, to obtain more pain relief and lessened adverse side effects.

It is, therefore, a primary object of the present invention to provide novel pharmaceutical compositions of matter for use in eliciting an analgesic or anti-inflammatory and musculoskeletal relaxing response, said composition comprising an effective analgesic or anti-inflammatory amount of a newer non-steroidal anti-inflammatory drug and an effective amount of a skeletal muscle relaxant. Typically, the active ingredients are further associated with a non-toxic pharmaceutically acceptable inert carrier therefrom.

It is a further object of the present invention to provide methods for the treatment of various skeletal muscle disorders in a mammal such as skeletal muscle spasms, certain orthopedic conditions, disk syndromes, low back pain and the like, said method comprising administering to said mammal preselected dosages of said non-steroidal anti-inflammatory drug and said skeletal muscle relaxant.

Another object of the present invention is to provide suitable unit dose forms of said composition comprising an effective amount of a non-steroidal anti-inflammatory drug and an effective amount of a skeletal muscle relaxant.

DETAILED DESCRIPTION OF THE INVENTION

More specifically, the applicants herein have surprisingly found that certain newer non-steroidal anti-inflammatory agents are ideally suited for use in a formulation with skeletal muscle relaxants by reason of their enhanced analgesic anti-inflammatory and antipyretic activity and low incidence of untoward side effects, particularly at the optimum dosages provided for in the present invention, in comparison to aspirin or acetaminophen.

The superiority of various of the non-narcotic analgesics belonging to the newer non-steroidal anti-inflammatory drug class in comparative studies with aspirin and acetaminophen is well documented in the literature.

Cooper in 1977 found that ibuprofen 400 mg had a greater peak effect and longer duration of action than aspirin 650 mg. Cooper, S. A., Needle, A. E., Kruger, G. O. 1977. "An Analgesic Relative Potency Assay Comparing Aspirin, Ibuprofen and Placebo. "*J. Oral Surg.* 35: 898–903. Cooper in another study in 1982 found 400 mg of ibuprofen to be more effective than aspirin 650 mg. Cooper, S. A., Engel, J., Ladov, M., Precheur, H., Rosenheck, A., Rauch, D. 1982. "Analgesic Efficacy of an Ibuprofen-codeine Combination." *Pharmacotherapy* 2: 162–67. Sunshine et al found ibuprofen to be significantly superior to aspirin in the relief of post-episiotomy pain. Sunshine, A. et al, *Clinical Pharmacology and Therapeutics,* 24: 254–250, 1983.

Dionne in 1982 found ibuprofen to be more effective than acetaminophen in delaying the onset and intensity of post operative dental pain. Dionne, R. A., Campbell, R. A., Cooper, S. A., Hall, D. L., Buckingham, B. "Suppression of Post operative Pain by Preoperative Administration of Ibuprofen in Comparison to Placebo, Acetaminophen and Acetaminophen Plus Codeine." *J. Clin. Pharmacol.* (In press).

Naproxen sodium 550 mg was compared with 650 mg of aspirin and was found to provide earlier and better pain relief than aspirin by Sevelius, H., *J. Clin. Pharmacol.* 20: 480–485, 1980. "Comparative Analgesic Effects of Naproxen Sodium, Aspirin and Placebo."

Both flurbiprofen 50 and 100 mg were significantly more effective than aspirin 600 mg. Flurbiprofen 25 mg was slightly less effective than aspirin 600 mg. Sunshine, A., Olson N. Z., Laska, E. M. Zighelboim, I., DeCastro, A., Desarrazin, C., *Pharmaco Ther.* 3: 177–181. "Analgesic Effect of Graded Doses of Flurbiprofen in Post-episiotomy Pain."

Silberman found suprofen 200 mg more effective than aspirin 650 mg for pain relief in the treatment of moderate to severe pain resulting from musculoskeletal pain. Silberman, H. M. "Multiple-Dose Comparison of Suprofen, Aspirin and Placebo in the Treatment of Musculoskeletal Pain." *Pharmacology* 27: S 1, 65–73 (1983).

The outstanding analgesic and anti-inflammatory properties of the non-steroidal anti-inflammatory drugs compared to aspirin or acetaminophen have prompted the widespread acceptance and usage of these newer non-narcotic analgesics, as single entities, for the treatment and management of acute and chronic pain and inflammatory states, notably rheumatoid arthritis and osteoarthritis. However, the utilization of these agents in skeletal muscle relaxant compositions has not heretofore been considered.

The non-steroidal anti-inflammatory drugs (NSAID's) for use in the pharmaceutical compositions and methods of use of the present invention may be selected from any of the following categories:

(1) the propionic acid derivatives;
(2) the acetic acid derivatives;
(3) the fenamic acid derivatives;
(4) the biphenylcarboxylic acid derivatives; and
(5) the oxicams.

Accordingly, the term "NSAID" as used herein is intended to mean any non-narcotic analgesic non-steroidal anti-inflammatory compound, including the pharmaceutically acceptable non-toxic salts thereof, falling within one of the five structural categories above but excluding aspirin, acetaminophen and phenacetin.

The specific compounds falling within the foregoing definition of the non-steroidal anti-inflammatory drugs for use in the present invention are well known to those skilled in the art and reference may be had to various literature reference sources for their chemical structures, pharmacological activities, side effects, normal dosage ranges, etc. See, for example, *Physician's Desk Reference*, 38th Edition, 1984 and *The Merck Index*, 9th Edition, Merck and Company, Rahway, New Jersey (1976) and *Cutting's Handbook of Pharmacology*, 7th Edition, Ed. T. Z. Csaky, M.D., and B. A. Barnes, Appleton-Century-Crofts, New York, 1984, Chapter 49: 604–638.

While some of the above-identified compounds are primarily used at the present time as anti-inflammatory agents and others are primarily used as analgesics, in fact all of the contemplated compounds have both analgesic and anti-inflammatory activity and can be used at appropriate dosage levels for either purpose in the compositions and methods of the present invention. The compounds in groups (1) through (4) typically contain a carboxylic acid function; however, those acids are sometimes administered in the form of their pharmaceutically acceptable salts, e.g. sodium salts.

The propionic acid derivatives for use herein include, but are not limited to, ibuprofen, naproxen, naproxen sodium, flurbiprofen, fenoprofen, fenbufen, ketoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be encompassed by this group. Representative members of the propionic acid group include ibuprofen, naproxen, flurbiprofen, fenbufen, fenoprofen, ibuprofen aluminum, ketoprofen, fluprofen and bucloxic acid. Structural formulas for these representative group members are set forth below:

PROPIONIC ACID DERIVATIVES

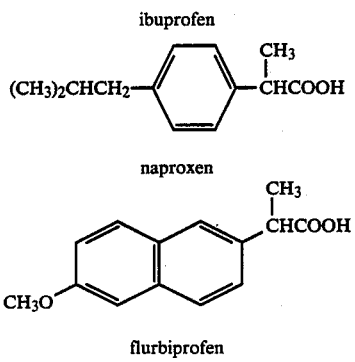

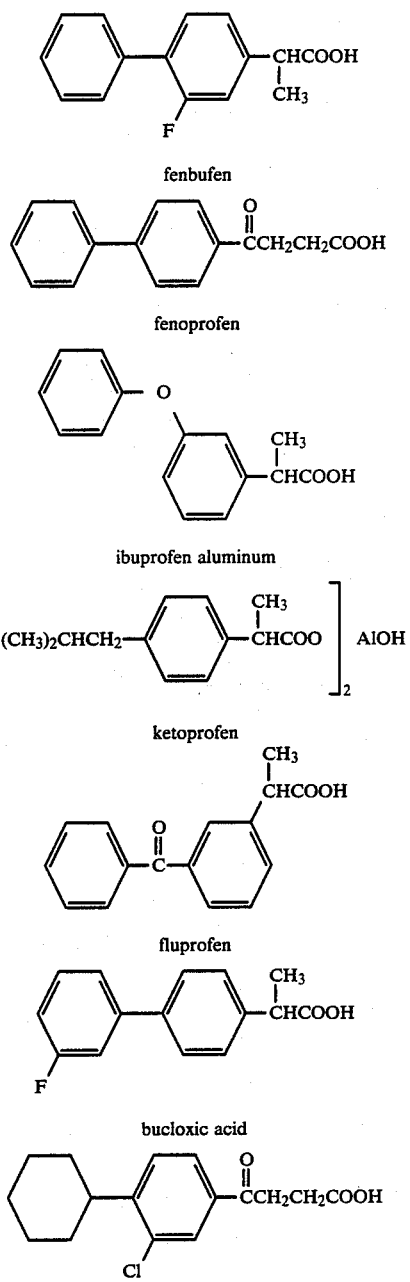

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g. —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives for use herein include, but are not limited to, indomethacin, sulindac, tolmetin, diclofenac, fenclofenac, alclofenac, ibufenac, isoxepac, furofenac, tiopinac, zidometacin, acemetacin, fentiazac, clidanac and oxepinac. Structurally related acetic acid derivatives having similar analgesic and anti-inflammatory properties are also intended to be encompassed by this group. Representative members of the acetic acid group include tolmetin, sulindac, indomethacin, diclofenac, alclofenac, fenclozic acid and ibufenac. Structural formulas for these representative group members are set forth below:

ACETIC ACID DERIVATIVES tolmetin sulindac indomethacin diclofenac alclofenac fenclozic acid ibufenac Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Representative members of the fenamic acid group include mefenamic acid, meclofenamate sodium (meclofenamic acid, sodium salt) and flufenamic acid. Structural formulas for representative group members are set forth below:

FENAMIC ACID DERIVATIVES mefenamic acid meclofenamic acid flufenamic acid

Thus, "fenamic acid derivatives" as defined herein are non-narcotic analgesics/non-steroidal anti-inflammatory drugs which contain the basic structure which can bear a variety of substituents and in which the free —COOH group can be in the form of a pharmaceutically acceptable salt group, e.g. —COO$^-$Na$^+$.

The biphenylcarboxylic acid derivatives for use herein include, but are not limited to, diflunisal and flufenisal. Structurally related biphenylcarboxylic acid derivatives having similar analgesic and anti-inflammatory properties are also intended to be encompassed by this group. Representative members of this group are diflunisal and flufenisal, whose structural formulas are set forth below:

BIPHENYLCARBOXYLIC ACID DERIVATIVES diflunisal flufenisal

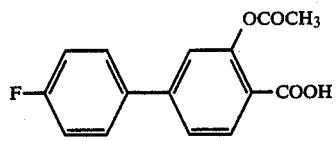

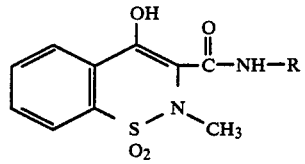

Thus, "biphenylcarboxylic acid derivatives" as defined herein are non-narcotic analgesics/non-steroidal anti-inflammatory drugs which contain the basic structure

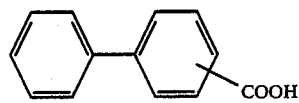

which can bear a variety of substituents and in which the free —COOH group can be in the form of a pharmaceutically acceptable salt group, e.g. —COO$^-$Na$^+$.

The oxicams for use herein include, but are not limited to, piroxicam, sudoxicam, isoxicam and CP-14,304. Structurally related oxicams having similar analgesic and anti-inflammatory properties are also intended to be encompassed by this group. Representative members of this group are depicted below:

OXICAMS piroxicam

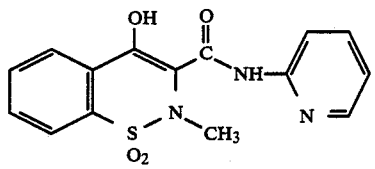

sudoxicam

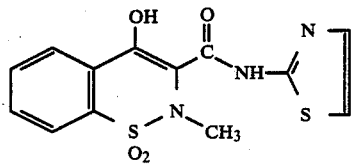

isoxicam

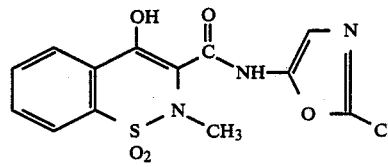

[4-hydroxy-1,2-benzothiazine 1,1-dioxide 4-(N—phenyl)-carboxamide]

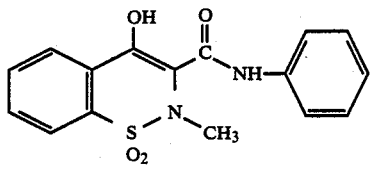

Thus, "oxicams" as defined herein are non-narcotic analgesics/non-steroidal anti-inflammatory drugs which have the general formula wherein R is an aryl or heteroaryl ring system.

Of the propionic acid derivatives for use herein, ibuprofen, naproxen, naproxen sodium, flurbiprofen, fenoprofen, ketoprofen, suprofen, fenbufen, and fluprofen may be mentioned as particularly preferred compounds.

Of the acetic acid derivatives, presently preferred members include tolmetin sodium, sulindac and indomethacin.

Of the fenamic acid derivatives, particularly preferred compounds include mefenamic acid and meclofenemate sodium.

The particularly preferred biphenylcarboxylic acid derivatives for use in the present invention include diflunisal and flufenisal.

The particularly advantageous oxicams include piroxicam, sudoxicam and isoxicam.

Of the foregoing non-steroidal anti-inflammatory drugs, in the practice of the preferred embodiments of the present invention, ibuprofen and naproxen are most preferred.

With respect to the dosage amount of the non-steroidal anti-inflammatory drugs in the formulations of the invention, although the specific dose will vary depending upon the age and weight of the patient, the severity of the symptoms, the incidence of side effects and the like, for humans, typical effective analgesic amounts of presently preferred NSAID's for use in unit dose compositions of the invention presented in milligrams are set forth in Table II; however, greater or lesser amounts may be employed if desired or necessary. A description of unit dose dispensing is presented in Remington's Pharmaceutical Sciences, Fifteenth Edition, pages 1698-9.

With respect to the compounds set forth hereinabove falling within the propionic acid derivative category, suitable dosage ranges for these compounds will generally fall within the range of about 12.5 mg to 900 mg in each unit dose. A general dosage range for those compounds that fall within the acetic acid derivative category is about 25 mg to 400 mg in each unit dose. A general dosage range for those compounds falling within the fenamic acid derivative category is about 50 mg to 500 mg in each unit dose. A general dosage range for those compounds falling within the biphenylcarboxylic acid derivative category is about 125 mg to 1000 mg in each unit dose. A general dosage range for those compounds falling within the oxicam category is about 10 mg to 40 mg in each unit dose.

TABLE II

| DRUG | PREFERRED UNIT DOSE | MAX. TOTAL DAILY DOSE | WIDE RANGE UNIT DOSE |
|---|---|---|---|
| Diflunisal | 125-500 | 1500 | 125-1000 |
| Ibuprofen | 100-400 | 2400 | 50-800 |
| Naproxen | 125-500 | 1250 | 125-750 |
| Flurbiprofen | 25-50 | 300 | 25-150 |
| Fenoprofen | 50-200 | 2400 | 50-300 |
| Piroxicam | 10-40 | 80 | 10-80 |
| Mefenamic Acid | 125-250 | 1250 | 125-500 |
| Fenbufen | 100-500 | 3000 | 100-900 |

TABLE II-continued

| DRUG | PREFERRED UNIT DOSE | MAX. TOTAL DAILY DOSE | WIDE RANGE UNIT DOSE |
|---|---|---|---|
| Ketoprofen | 25–150 | 1200 | 25–200 |
| Naproxen Sodium | 138–550 | 1375 | 138–825 |
| Suprofen | 100–400 | 1600 | 50–600 |

A complete description of the various NSAID's, including acceptable analgesically effective amounts thereof for use in unit dose compositions of the present invention also appears in applicants co-pending U.S. application Ser. No. 578,288, filed Feb. 8, 1984 and U.S. Pat. No. 4,486,436, the entire disclosures of which are incorporated herein by reference.

The term "skeletal muscle relaxant" as used herein is intended to mean any compound having skeletal muscle relaxing properties. Any skeletal muscle relaxant is useful in the practice of the present invention. The skeletal muscle relaxants may be broadly classified as those that act directly on skeletal muscle and those that act on the level of the central nervous system. The centrally-acting muscle relaxants block impulses at the interneurons of polysynaptic reflex arcs, mainly at the level of the spinal cord. This is demonstrated by the abolishment of the diminution of the flexor and crossed extensor reflexes which possess one or more interneurons between the sensory and motor fibers. The knee-jerk response, which acts through a monosynaptic reflex system and therefore possesses no interneurons is unaffected by this class of drugs.

These drugs also possess mild depressant properties on the CNS; the major sites of action are the brain stem and subcortical areas. The ascending reticular formation, which receives and transmits some sensory stimuli, transmits and maintains a state of arousal. When the passage of stimuli is blocked at the level of ascending reticular formation, response to sensory stimuli is reduced and depression ranging from sedation to anesthesia may occur. Suppression of polysynaptic reflexes at the spinal cord level is not sufficient to account for depression of the arousal system.

Most of the clinically useful centrally acting skeletal muscle relaxants fall into the following chemical groups: glycerylmonoethers and derivatives, oxazoles, substituted alkanediols, benzazoles, benzodiazepines, and miscellaneous. Since not all of the skeletal muscle relaxants readily lend themselves to such categorization, a miscellaneous category is required.

The formulations of the present invention comprise, in addition to the non-steroidal anti-inflammatory drugs, at least one active ingredient from the above-described chemical groups. Typical examples of drugs contained within each chemical group are presented below:

a. glycerylmonoethers and derivatives
   mephenesin
   mephenesin carbamate
   mephenesin acid succinate
   methocarbamol
   chlorphenesin carbamate
b. oxazoles
   mephenoxalone
   metaxalone
c. substituted alkanediols
   meprobamate
   carisoprodol
d. benzazoles
   zoxazolamine
   chlorzoxazone
e. benzodiazepines
   chlordiazepoxide HCl
   diazepam
f. miscellaneous
   analexin
   baclofen
   chlormezanone
   cyclobenzaprine HCl
   orphenadrine citrate Some centrally-acting muscle relaxants are presented in Table III along with their chemical structure, dosage forms and usual unit dose.

TABLE III

Centrally-Acting Skeletal Muscle Relaxants

| GENERIC NAME | CHEMICAL STRUCTURE | DOSAGE FORMS* | USUAL UNIT DOSE |
|---|---|---|---|
| Baclofen | Cl—C6H4—CHCH2COOH / CH2NH2 | T:10 mg | 5–20 mg |
| Carisoprodol | H2NCOOCH2C(CH2CH2CH3)(CH3)CH2OOCNHCH(CH3)2 | T:350 mg | 350 mg |
| Chlorphenesin carbamate | Cl—C6H4—OCH2CHCH2OOCNH2 with OH | T:400 mg | 800 mg |
| Chlorzoxazone | Cl—C6H3—O—C(=O)—NH (benzoxazolone) | T:250 mg | 250–750 mg |

TABLE III-continued
Centrally-Acting Skeletal Muscle Relaxants

| GENERIC NAME | CHEMICAL STRUCTURE | DOSAGE FORMS* | USUAL UNIT DOSE |
|---|---|---|---|
| Cyclobenzaprine Hydrochloride, U.S.P. | (tricyclic structure with =CHCH$_2$CH$_2$N(CH$_3$)$_2$, ·HCl) | T:10 mg | 10 mg |
| Diazepam | (benzodiazepine structure with CH$_3$, Cl, phenyl, N, O) | T:2,5,10 mg<br>I:5 mg/ml | 2-10 mg oral<br>2-15 mg i.m. or i.v. |
| Mephenesin | (CH$_3$-phenyl-OCH$_2$CH(OH)CH$_2$OH) | T:500 mg | 1-2 g |
| Metaxalone | (3,5-(H$_3$C)$_2$-phenyl-OCH$_2$-oxazolidinone) | T:400 mg | 800 mg |
| Methocarbamol, U.S.P. | (OCH$_3$-phenyl-OCH$_2$CH(OH)-CH$_2$OOCNH$_2$) | T:500,750 mg<br>I:100 mg/ml | 1-2 g. oral<br>1-3 g. i.v., slowly |
| Orphenadrine Citrate, U.S.P. | (diphenyl-COCH$_2$CH$_2$-$^+$NH(CH$_3$)$_2$·HOC(CH$_2$CO$^-$)(CH$_2$COH)COOH with 2-CH$_3$) | T:100 mg<br>I:30 mg/ml | 100 mg. oral<br>60 mg. i.m. or i.v. |

*T = tablet; I = injection.

Mephensin has been the most extensively studied drug among the skeletal muscle relaxants. Although rarely used today it is a prototype for other skeletal muscle relaxants which have similar pharmacological actions. These include carisoprodol, chlorphenesin carbamate, chlorzoxazone, metaxalone, methocarbamol and orphenadrine citrate. Methocarbamol and orphenadrine citrate can be administered either orally or intravenously. In the latter case, it is used to relieve severe, acute muscle spasm of local origin caused by inflammation or trauma. Other clinically useful skeletal muscle relaxants which differ from mephensin in their pharmacological mode of action are the benzodiazepines (e.g., diazepam), baclofen and cyclobenzaprine. Diazepam and other benzodiazepines are used for a variety of spastic states but may be most useful in painful spasms of flexor muscles.

These drugs appear to have a more selective action on reticular neuronal mechanisms that control muscle tone than on spinal interneuronal activity, whereas mephensin-like drugs exhibit no such selectivity. Baclofen is used for the treatment of spasticity in patients with multiple sclerosis. Baclofen's usefulness is limited by its adverse effects which include drowsiness, insomnia, dizziness, etc. Cyclobenzaprine is closely related to the tricyclic antidepressants both structurally and pharmacologically and has side effects which are common with that group of drugs.

In addition to the centrally-acting muscle relaxants identified above, dantrolene is a typically non-centrally-acting muscle relaxant which exerts its effects by direct actions on skeletal muscle. Dantrolene has the following chemical structure:

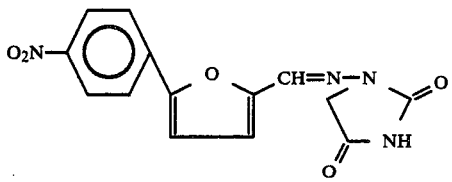

Dantrolene reduces contraction of skeletal muscle by direct action on excitation-contraction coupling, perhaps by decreasing the amount of calcium released from the sarcoplamic reticulum. Although dantrolene produces some central nervous system depressant effects, it does not impair polysynaptic reflexes preferentially as do the centrally-acting muscle relaxants. Dantrolene sodium is available for oral use at 25-100 mg in a single dose or for intravenous administration up to a total of 10 mg/kg.

The preferred muscle relaxants intended for use in the practice of the present invention include diazepam, carisoprodol, chlorzoxazone, methocarbamol and orphenadrine citrate.

With respect to the dosage amount of the skeletal muscle relaxant in the formulations of the invention, although the specific dose will vary depending upon the age and weight of the patient, the severity of the symptoms, the incidence of side effects and the like, for humans, typical effective amounts of the presently preferred skeletal muscle relaxants for use in unit dose compositions of the invention are about 2-10 mg diazepam, 100-600 mg carisoprodol, 100-1000 mg chlorzoxazone, 200-2000 mg methocarbamol and 25-100 mg orphenadrine citrate.

For those compounds not indicated as members of the preferred category their typical or suggested ranges of unit dose administration are well-known to those in the art. The package insert of each product sets out the dosage ranges determined by the manufacturer. These dosage ranges are the general guidelines followed by those familiar with skeletal muscle relaxants.

The skeletal muscle relaxant may be centrally-acting or it may directly affect skeletal muscle tissue. The skeletal muscle relaxant may fall within one of the five structural categories indicated hereinabove.

Several commercial centrally-acting skeletal muscle relaxants are currently available in the United States in formulations with aspirin or acetaminophen. The list of these currently available combination products is presented in Table I. These products are intended to provide an analgesic component to help relieve both the pain and in some cases the anxiety of the pain experience. Elenbass reviewed the published studies of such combination products in *American Journal of Hospital Pharmacy*, Vol. 37, October 1980, pages 1313-1323. He concluded that the combination products provide ingredients to treat both the spasm and pain associated with musculoskeletal disorders, and they appear to provide better symptom relief than the individual agents. The *AMA Drug Evaluations*, 5th Ed., page 103 comment that results of some studies have alleged that a combination of muscle relaxant and an analgesic provides greater benefit in patients with acute musculoskeletal problems than similar doses of analgesic alone. The same page of *AMA Drug Evaluations* lists examples of combination skeletal muscle relaxants and analgesics.

Surprisingly, the present inventors now find that, the newer non-steroidal anti-inflammatory drugs, which differ substantially in chemical structure from aspirin, acetaminophen and phenacetin, and which have significantly different biological profiles therefrom can be advantageously formulated into a novel composition together with a skeletal muscle relaxant and administered to mammals, especially to humans, to obtain more pain relief and lessened adverse side effects.

Certain NSAID's are particularly long-acting and need be administered less frequently than the usual every 4 to 6 hours; for example, diflunisal and naproxen are typically administered only twice daily and piroxicam only once a day. When such long-acting drugs are employed, it is often desirable to include an additional amount of a muscle relaxant in the composition in sustained release form.

Typical therapeutically active components of the present invention, along with their usual adult dosage, for use in the pharmaceutical compositions and methods of the present invention are set forth in the following Table IV.

Illustrative of typical unit dose forms are tablets or capsules containing the amounts indicated in Table IV. Note that the asterisk (*) indicates that the adjacent amount is in sustained release form, e.g. "130 mg+130 mg*" means that the first 130 mg is formulated for immediate release, while the second 130 mg is in sustained release form.

TABLE IV

| Typical Unit Doses | |
|---|---|
| Skeletal Muscle Relaxant | NSAID |
| diazepam | ibuprofen |
| 2 mg | 100 mg |
| 5 mg | 200 mg |
| 10 mg | 400 mg |
| diazepam | naproxen |
| 2 mg + 2 mg* | 125 mg |
| 5 mg + 5 mg* | 250 mg |
| 10 mg + 10 mg* | 500 mg |
| diazepam | fenoprofen |
| 2 mg | 100 mg |
| 5 mg | 200 mg |
| 10 mg | 200 mg |
| chlorzoxazone | ibuprofen |
| 250 mg | 200 mg |
| 500 mg | 400 mg |
| chlorzoxazone | naproxen |
| 250 mg + 250 mg* | 125 mg |
| 500 mg + 500 mg* | 250 mg |
| 500 mg + 500 mg* | 500 mg |
| chlorzoxazone | fenoprofen |
| 250 mg | 100 mg |
| 500 mg | 200 mg |
| chlorzoxazone | piroxicam |
| 250 mg + 250 mg* | 20 mg |
| 500 mg + 500 mg* | 20 mg |
| carisoprodol | ibuprofen |
| 200 mg | 200 mg |
| 400 mg | 400 mg |
| carisoprodol | naproxen |
| 200 mg + 200 mg* | 125 mg |
| 200 mg + 200 mg* | 250 mg |
| 400 mg + 400 mg* | 500 mg |
| carisoprodol | diflunisal |
| 200 mg + 200 mg* | 250 mg |
| 200 mg + 200 mg* | 500 mg |
| 400 mg + 400 mg* | 500 mg |
| methocarbamol | ibuprofen |
| 400 mg | 200 mg |
| 800 mg | 400 mg |
| methocarbamol | naproxen |
| 400 mg + 400 mg* | 125 mg |
| 400 mg + 400 mg* | 250 mg |
| 800 mg + 800 mg* | 500 mg |
| methocarbamol | sulindac |

TABLE IV-continued

| Typical Unit Doses | |
|---|---|
| | NSAID |
| 400 mg + 400 mg* | 150 mg |
| 800 mg + 800 mg* | 200 mg |
| orphenadrine citrate | ibuprofen |
| 25 mg | 200 mg |
| 50 mg | 400 mg |
| orphenadrine citrate | naproxen |
| 25 mg + 25 mg* | 125 mg |
| 25 mg + 25 mg* | 250 mg |
| 50 mg + 50 mg* | 500 mg |
| orphenadrine citrate | ketoprofen |
| 25 mg | 25 mg |
| 50 mg | 50 mg |

In accordance with the practices of the present invention, the NSAID/skeletal muscle relaxant compositions, may be administered in admixture with suitable pharmaceutical diluents, carriers or other excipients (collectively referred to as "carrier" materials) suitably selected with respect to the intended route of administration and conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodiumbenzoate, sodium acetate, sodium chloride, etc. Disintegrators include, without limitation, starch, methylcellulose, agar, bentonite, guar gum, etc. Sweetening and flavoring agents and preservatives can also be included where appropriate.

Of course, additionally, the compositions of the present invention may be formulated in sustained release form to provide the rate controlled release of any one or more of the components to optimize the therapeutic effects, i.e., analgesia, skeletal muscle relaxation, etc. while minimizing undesirable side effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Similarly, injectable dosage units may be utilized to accomplish intravenous, intramuscular or subcutaneous administration and, for such parenteral administration, suitable sterile aqueous or non-aqueous solutions or suspensions, optionally containing appropriate solutes to effectuate isotonicity, will be employed.

The pharmaceutical compositions of the present invention may also be formulated and administered by other methods which are known for administering analgesics. The composition may be adapted for rectal administration, for example, as a suppository. The composition may also be adapted for topical application, for example, the composition may be applied in a pharmaceutically acceptable topical vehicle selected from the group consisting of creams, gels, ointments, powders, aerosols and solutions suitable for topical administration.

As representative suitable formulations consistent with the objects, features and advantages of the present invention, the following non-limiting examples are provided.

EXAMPLE 1

Chlorzoxazone—250 mg
Ibuprofen—400 mg
Triturate active ingredients and q.s. with lactose to selected capsule size

EXAMPLE 2

Methocarbamol—400 mg
Fenoprofen—200 mg
Triturate active ingredients and q.s. with lactose to selected capsule size From the foregoing, other typical acceptable pharmaceutical formulations will be apparent to those skilled in the art of pharmaceutical formulations.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove with respect to the active ingredients may be applicable as a consequence of variations of the responsiveness of the mammal treated, severity of symptoms, dosage related adverse effects, if any, observed and similar considerations. Accordingly, such expected variations or differences in the practice of the present invention and the results obtained are contemplated in accordance with the objects and practices of the present invention. It is intended, therefore, that the invention be limited only by the scope of the claims which follow.

What we claim is:

1. A method for the treatment of musculoskeletal disorders in a mammalian organism in need of such treatment, comprising administering to such organism a symptom relieving analgesically and anti-inflammatorily effective amount of (i) at least one of the propionic acid NSAIDs, ibuprofen, naproxen, benoxaprofen, flurbiprofen, fenoprofen, fenbufen, ketoprofen, indoprofen, pirprofen, carprofen, oxaprozin, pranoprofen, miroprofen, ibuprofen aluminum, tioxaprofen, suprofen, alminoprofen, tiaprofenic acid, fluprofen, bucloxic acid, or pharmaceutically acceptable salt thereof, in combinatory immixture with a skeletal muscle relaxing amount of (ii) at least one of the glycerylmonoether SMRS, methocarbamol, mephenesin, mephenesin carbamate, mephenesin acid succinate, chlorphenesin carbamate, or pharmaceutically acceptable salt thereof.

2. The method for the treatment of musculoskeletal disorders as defined by claim 1, said NSAID (i) comprising ibuprofen, naproxen, flurbiprofen, fenoprofen, ketoprofen, suprofen, fenbufen, fluprofen, or pharmaceutically acceptable salt thereof.

3. The method for the treatment of musculoskeletal disorders as defined by claim 2, said NSAID (i) comprising ibuprofen or pharmaceutically acceptable salt thereof.

4. The method for the treatment of musculoskeletal disorders as defined by claim 2, said NSAID (i) comprising naproxen or pharmaceutically acceptable salt thereof.

5. The method for the treatment of musculoskeletal disorders as defined by claim 2, said NSAID (i) comprising ketoprofen or pharmaceutically acceptable salt thereof.

6. The method for the treatment of musculoskeletal disorders as defined by claim 1, said SMR (ii) comprising methocarbamol or pharmaceutically acceptable salt thereof.

7. The method for the treatment of musculoskeletal disorders as defined by claim 1, said combinatory immixture further comprising a pharmaceutically acceptable non-toxic carrier, diluent or excipient.

8. The method for the treatment of musculoskeletal disorders as defined by claim 1, comprising oral administration of a unit dosage amount of said combinatory immixture.

9. The method for the treatment of musculoskeletal disorders as defined by claim 1, comprising parenteral administration of a unit dosage amount of said combinatory immixture.

10. The method for the treatment of musculoskeletal disorders as defined by claim 1, comprising rectal administration of a unit dosage amount of said combinatory immixture.

11. The method for the treatment of musculoskeletal disorders as defind by claim 1, said combinatory immixture comprising from about 12.5 mg to 900 mg of said NSAID (i).

12. The method for the treatment of musculoskeletal disorders as defined by claim 6, said combinatory immixture comprising from about 200 mg to 2000 mg of said methocarbamol SMR or pharmaceutically acceptable salt thereof.

13. The method for the treatment of musculoskeletal disorders as defined by claim 3, said combinatory immixture comprising from about 100 mg to 400 mg of ibuprofen or pharmaceutically acceptable salt thereof.

14. The method for the treatment of musculoskeletal disorders as defined by claim 1, comprising sustainedly controlledly administering a unit dosage amount of said combinatory immixture.

15. The method for the treatment of musculoskeletal disorders as defined by claim 1, comprising eliciting a musculoskeletal relaxing and analgesic/anti-inflammatory response in a mammalian organism afflicted with muscle spasms and the symptoms of rheumatoid arthritis.

16. The method for the treatment of musculoskeletal disorders as defined by claim 1, comprising eliciting a musculoskeletal relaxing and analgesic/anti-inflammatory response in a mammalian organism afflicted with muscle spasms and the symptoms of osteoarthritis.

17. The method for the treatment of musculoskeletal disorders as defined by claim 1, comprising eliciting a musculoskeletal relaxing and analgesic/anti-inflammatory response in a mammalian organism afflicted with skeletal muscle spasms.

18. The method for the treatment of musculoskeletal disorders as defined by claim 1, comprising eliciting a musculoskeletal relaxing and analgesic/anti-inflammatory response in a mammalian organism afflicted with lower back pain.

19. The method for the treatment of musculoskeletal disorders as defined by claim 1, comprising eliciting a musculoskeletal relaxing and analgesic/anti-inflammatory response in a mammalian organism afflicted with disk syndrome.

* * * * *